United States Patent [19]

Basser

[11] Patent Number: 5,125,408
[45] Date of Patent: Jun. 30, 1992

[54] PRESSURE SENSOR ELEMENT AND METHOD TO MEASURE CONTACT STRESS

[75] Inventor: Peter J. Basser, Washington, D.C.

[73] Assignee: The United States of America as represented by the of the Department of Health and Human Services, Washington, D.C.

[21] Appl. No.: 769,418

[22] Filed: Sep. 19, 1991

Related U.S. Application Data

[60] Continuation of Ser. No. 07/535,616, Jun. 11, 1990, abandoned, which is a division of Ser. No. 07/261,303, Oct. 24, 1988, Pat. No. 4,967,764.

[51] Int. Cl.$^5$ .............................................. A61B 5/055
[52] U.S. Cl. .................................. 128/653.2; 128/748; 128/774
[58] Field of Search ............... 128/653.2, 653.4, 653.5, 128/654, 782, 748, 774

[56] References Cited

U.S. PATENT DOCUMENTS

| | | |
|---|---|---|
| 2,566,369 | 9/1951 | Putman . |
| 3,911,902 | 10/1975 | Delpy . |
| 3,958,562 | 5/1976 | Hakim et al. . |
| 3,977,391 | 8/1976 | Fleischmann . |
| 4,124,023 | 11/1978 | Fleischmann et al. . |
| 4,186,749 | 2/1980 | Fryer . |
| 4,246,908 | 1/1981 | Inagaki et al. . |
| 4,393,878 | 7/1983 | Kahn . |
| 4,627,443 | 12/1986 | Chubbuck et al. . |
| 4,649,447 | 3/1987 | Gries et al. ........................... 128/654 |
| 4,660,568 | 4/1987 | Cosman . |
| 4,729,892 | 3/1988 | Beall .................................... 128/654 |
| 4,738,267 | 4/1988 | Lazorthes et al. . |
| 4,774,957 | 10/1988 | Nambu et al. .................. 128/653 A |

*Primary Examiner*—Ruth S. Smith
*Attorney, Agent, or Firm*—Lowe, Price, LeBlanc & Becker

[57] ABSTRACT

A biological implantable pressure sensor element comprises a fixed volume pouch formed by a sealed, flexible, impermeable membrane comprising therewithin a gel mass contained in a gel volume, said gel being hydrated with an aqueous solution comprising an agent having at least a first and a second NMR-detectable form, the proportion of the first to the second form of the agent in the gel volume being determined by their electrolytic interaction with the gel, whereby when an external pressure is applied to the sensor element a d (chemical shift)/d($\sigma$/K) greater than 0.0001 ppm is attained, wherein $\sigma$ is the external pressure and K is the modulus of the gel. A kit contains sterile, individually wrapped sensor elements.

A method of measuring in vivo contact stress applied to an implanted pressure sensor element, comprises implanting the pressure sensor of the invention into a situs of a subject in need of such measurement, non-invasively subjecting the subject situs to a nuclear magnetic resonance source effective to detect said NMR-detectible agent, obtaining the NMR spectrum of said agent, obtaining the chemical shifts from the spectrum, repeating steps (b) to (d) at least once at a desired time interval, comparing the chemical shifts obtained in step (d) at different time intervals, and calculating the contact stress applied to said sensor element at a desired time from a correlation of observed chemical shifts for normalized stresses ($\sigma$/K) for the sensor element.

A method of measuring in vitro contact stress applied to a pressure sensor element, comprises placing the stress sensor element of the invention in contact with a biological tissue in culture, non-invasively subjecting the biological tissue to a nuclear magnetic resonance source effective to detect said NMR-detectible agent, obtaining the NMR spectrum of said agent, obtaining the chemical shifts from the spectrum, repeating steps (b) to (d) at least once at a desired time interval, comparing the chemical shifts obtained in step (d) at different time intervals, and calculating the contact stress applied to said sensor element of a desired time from a correlation of observed chemical shifts to normalized stresses ($\pi$/K) for the sensor element.

15 Claims, 8 Drawing Sheets

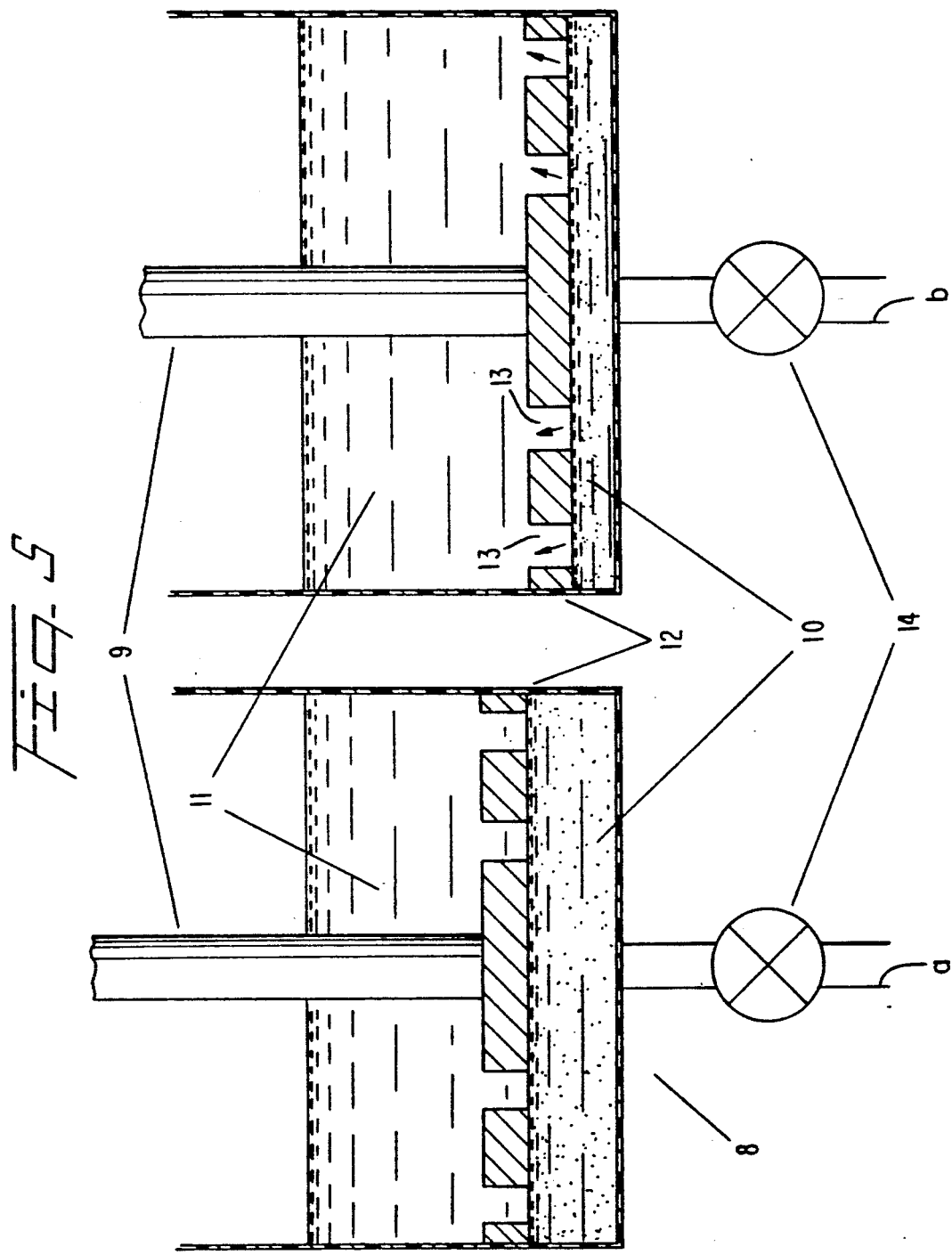

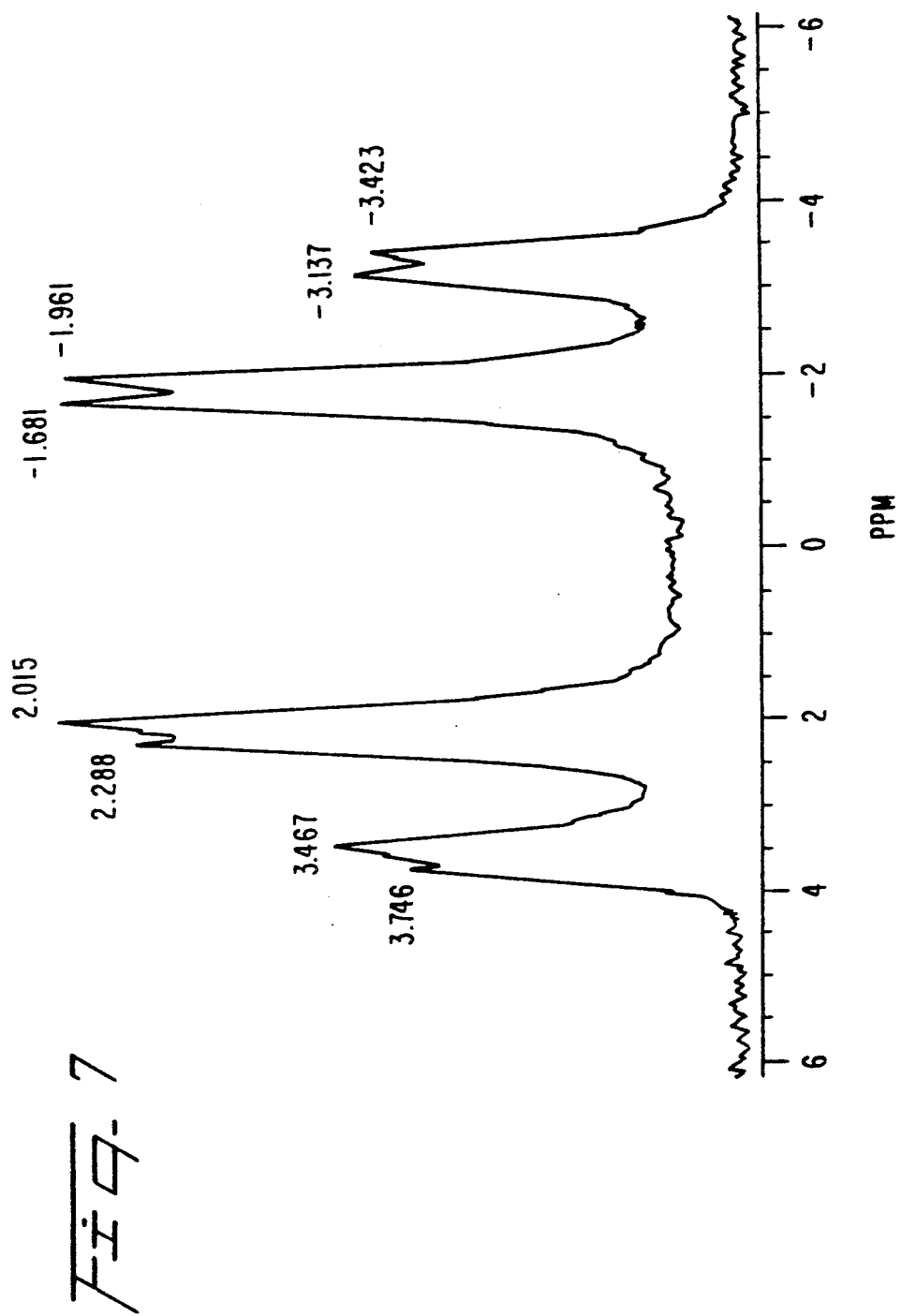

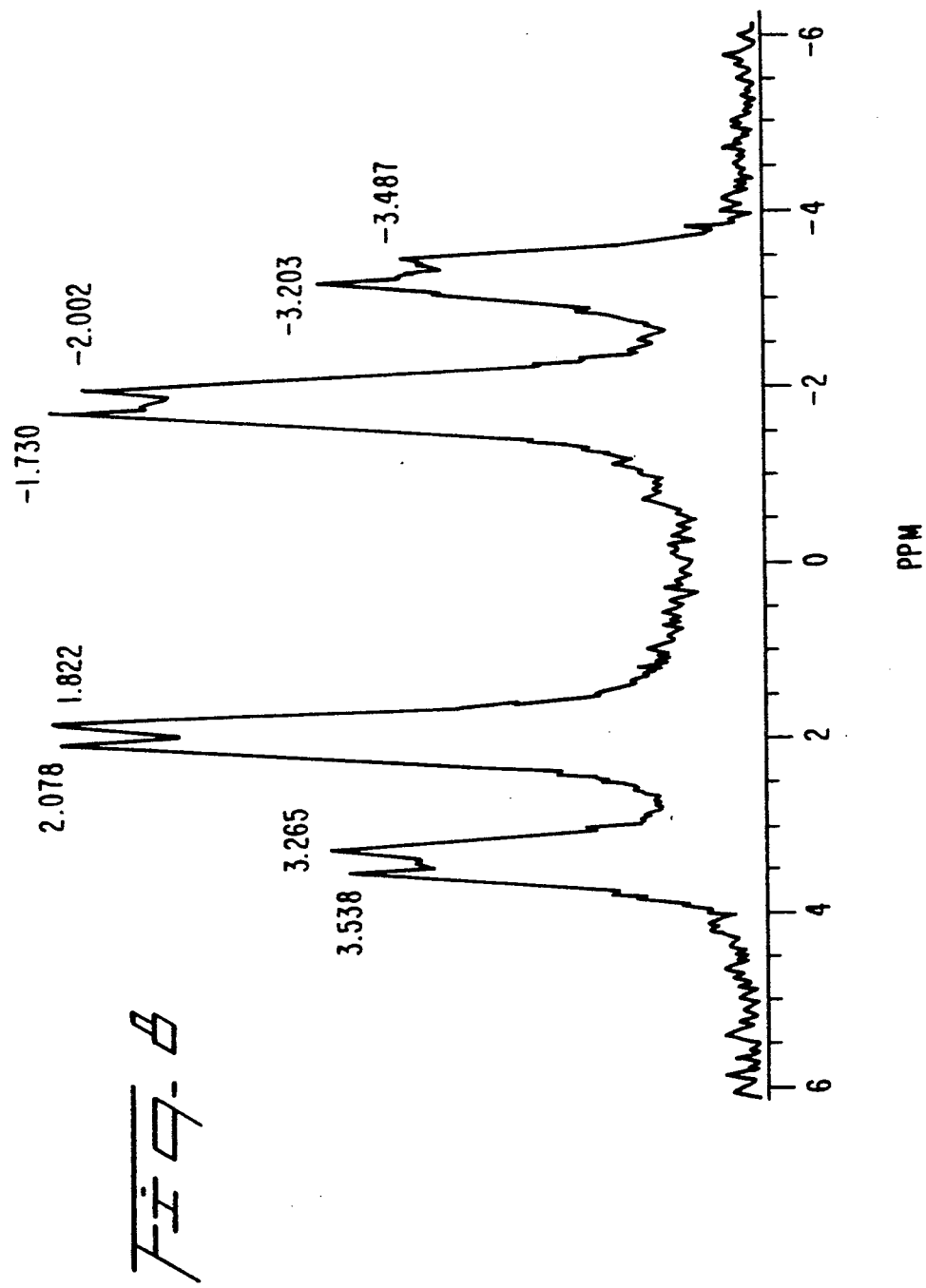

PRESSURE SENSOR ELEMENT AND METHOD TO MEASURE CONTACT STRESS

This application is a Continuation application of application Ser. No. 07/535,616, filed Jun. 11, 1990 now abandoned, which is a divisional application of application Ser. No. 07/261,303, filed Oct. 24, 1988 U.S. Pat. No. 4,967,764.

BACKGROUND OF THE INVENTION

This invention relates to an implantable pressure sensor element utilizing non-invasive NMR spectroscopy as a measuring tool. The sensor element requires no external connections and releases no toxic substances into the host system. The sensor element may be utilized for the in vitro as well as in vivo measurement of the normal component of tissue stress. The present invention finds its use in numerous applications among which are medical applications and biotechnology applications.

Elevated levels of mechanical stress may induce tissue trauma by reducing perfusion or compromising structural integrity. When tissue is compressed such as when a growing tumor displaces the tissue, the capillary volume in the region is reduced. This, in general, causes a concomitant reduction in blood perfusion to the area. Additional compression may cause the development of nerve pinching, microtears and other structural defects. If the capillary pressure increases while the surrounding tissue is confined by rigid or indistensible walls trauma may also result. A good example of the latter is the case of cardiac or brain edemas where increased fluid volume occurs at the expense of decreased tissue volume. Either condition may cause damage to vital biological structures. This is also true of stresses applied to other parts of the human body. The stress developed within the tissue that causes this damage is called the mechanical contact stress. Contact stress is defined as the normal component of the interfacial stress between two bodies It should be remarked that contact stress within the context of this invention is not the hydrostatic pressure.

In situations where the monitoring of pressure is necessary such as those encountered in the biomedical arts it is desirable to have a device which is entirely implantable within the body of the subject. Many prior art devices provided for this purpose are transcutaneous, that is, a portion of the device extends outside of the subject's body. These devices have the drawback that they have a high incidence of infection at the point where the device emerges from the subject's body. In addition, in many instances cables emerging from the subject's body limit the mobility of a patient (e.g., U.S. Pat. Nos. 4,660,568, 4,246,908, 4,393,878, 4,186,749 and 4,738.267, French Patent Nos. 2,455,735, 2,384,482, 2,274,261 and 2,262,953 and German Patent No. 1,965,231, among others).

Other prior art devices are known which are fully implantable and do not require any connectors to emerge through the skin of a subject's body. These devices are implantable electronic devices which are interrogated by induction or which transmit coded information to an appropriate monitor. In many instances they contain complex precision electronic equipment which must be implanted, e.g., inside the head of a subject, and require high expenditures, and sophisticated monitoring apparatuses (e.g., U.S. Pat. Nos. 3,977,391, 4,124,023, 4,006,734, 3,911,902 and 2,566,369, among others).

Other devices are also known which utilize radiopaque materials which are mechanically shifted in proportion to changes in pressure once the device is implanted. One such example is the X-ray opaque device described in U.S. Pat. No. 4,627,443. Another such device is described in U.S. Pat. No. 4,660,568. This patent provides an intracranial implantable sensor which undergoes a conformational change with pressure and is coupled through the skin by electromagnetic, acoustic or mechanical transmission to an external device which detects the change and interprets the pressure. This sensor has an insulating body with a moveable element which oscillates along an opening or channel in the body of a subject. The element communicates with the external atmospheric pressure by means of a membrane which is nearly coplanar with the intact skin covering it and on the other side with the internal pressure by another membrane. The degree of the moveable element's displacement relative to the body of the subject is correlated with the difference in the internal and atmospheric pressures.

A further type of implantable pressure sensor element is that provided by U.S. Pat. No. 3,958,562. This sensor element comprises a silicone rubber vessel, the walls of which have wax trapped therewithin, which is filled with a non-toxic hydraulic fluid compatible with body fluids However, this pressure sensor has attached thereto a piece of transcutaneous tubing for conducting out displaced liquid which may operate as a bellows.

A further implantable device is that described in U.S. Pat. No. 4,340,038 which operates as a magnetic field concentrator and may function for instance as an intracranial pressure monitoring device. The implanted sensor has a magnetic field pick-up which when placed next to an external magnetic field generator is capable of converting magnetic energy to electrical energy for energizing the device. The device contains a ferrite material and is adapted to operate in response to energy provided by an externally located magnetic field generator.

Thus, there is still a need for further development of biocompatible implantable devices which are capable of fast measuring of contact pressure by non-invasive means.

SUMMARY OF THE INVENTION

This invention relates to a biological implantable contact pressure sensor element comprising a fixed volume pouch formed by a sealed, flexible, impermeable membrane comprising therewithin a gel mass contained in a gel volume, said gel being hydrated with an aqueous solution comprising an NMR-detectable agent, whereby when an external contact pressure is applied to the sensor element a d(chemical shift)/d($\sigma$/K) greater than about 0.0001 ppm is attained, wherein $\sigma$ is the external contact pressure and K is the modulus of the gel.

A kit is also part of the invention comprising preferably 1 to 100 sensor elements in accordance with the invention, which may be sterilized and individually wrapped.

This invention also relates to a method of measuring in vivo contact stress applied to an implanted pressure sensor element comprising:

(a) implanting the pressure sensor of this invention into a situs of a subject in need of such measurement;

(b) non-invasively subjecting the subject situs to a system capable of measuring the nuclear magnetic resonance spectrum of said NMR-detectible agent;

(c) obtaining the NMR spectrum of said agent;

(d) obtaining the chemical shifts from the spectrum;

(e) repeating steps (b) to (d) at least once at a desired time interval;

(f) comparing the chemical shifts obtained in step (d) at different time intervals; and (g) calculating the contact stress applied to said sensor element at a desired time from a calibration curve relating observed chemical shifts to the normalized stress ($\sigma/K$) for the sensor element.

Also part of the invention is a method of measuring in vitro contact stress applied to a pressure sensor element, comprising (a) placing the stress sensor element of the invention in contact with a biological tissue in culture;

(b) non-invasively subjecting the biological tissue to a system capable of measuring the nuclear magnetic resonance spectrum of said NMR-detectible agent;

(c) obtaining the NMR spectrum of said agent;

(d) obtaining the chemical shifts from the spectrum;

(e) repeating steps (b) to (d) at least once at a desired time interval;

(f) comparing the chemical shifts obtained in step (d) at different time intervals; and (g) calculating the contact stress applied to said sensor element at a desired time from a calibration curve relating observed chemical shifts to the normalized stress ($\sigma/K$) for the stress element.

A more complete appreciation of the invention and many of the attendant advantages thereof will be readily perceived as the same becomes better understood by reference to the following detailed description when considered in connection with the accompanying figures.

BRIEF DESCRIPTION OF DRAWINGS

FIG. 5 shows a test device built in accordance with the present invention. The end of a 20 cm³ plastic syringe is sealed with paraffin tape. Holes are drilled through its rubber tamper so that fluid can flow through it when the plunger is depressed. The syringe is filled with gel and the indicator solution and then placed in an RF coil in the core of the magnet. Initially, no compressive force is applied to the plunger. Fluorine and proton NMR spectra are obtained. The same sample is then subjected to an applied compressive force of approximately 1.0 Newton or a calculated mean stress of 0.32 N/cm². The gel is allowed to equilibrate for about 1 hour prior to performing a second measurement. The total volume of polymer and solvent is maintained constant in both experiments as it is in the sensor element.

FIG. 7 shows the fluorine NMR spectrum of the uncompressed sensor element shown in FIG. 5.

FIG. 8 shows the fluorine NMR spectrum of the compressed sensor element described in FIG. 5.

Figure 1:
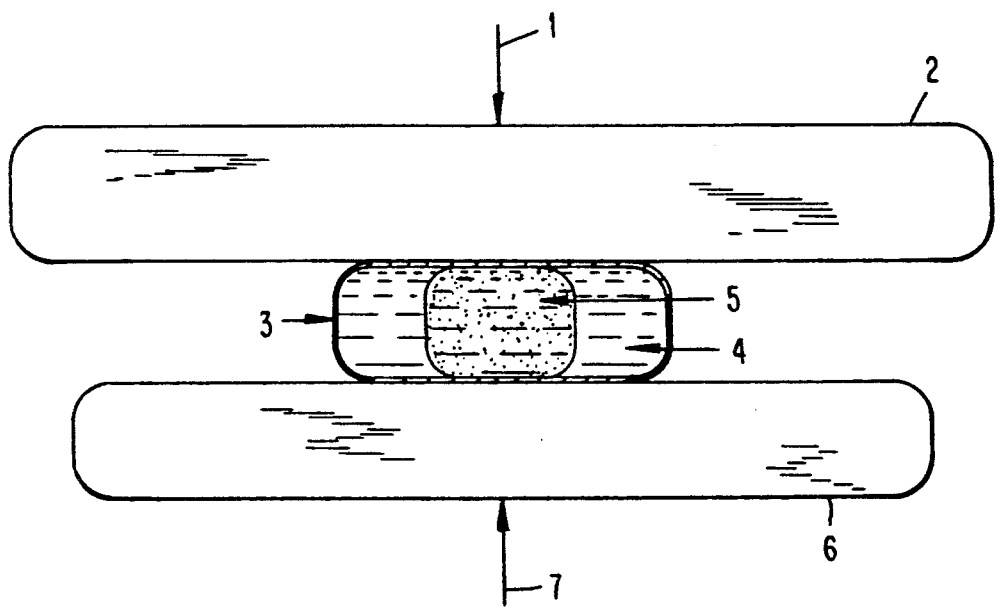
FIG. 1 shows a sensor element in accordance with the invention which consists of an impermeable but flexible pouch containing a polyelectrolyte gel bathed in an aqueous solution.

The split peaks observed in the spectra of FIGS. 7 and 8 are characteristic spectra lines of the fluorine moiety. However, the changes in the relative spacing between peaks does reflect a change in the pH of the interstitial and external solutions.

Other objects, advantages and features of the present invention will become apparent to those skilled in the art from the following discussion.

DESCRIPTION OF THE PREFERRED EMBODIMENTS

The present invention arose from a desire by the inventor to provide a novel sensor element in vivo as well as in vitro methods of measuring contact stress which were fully implantable, needed no external connectors and are inexpensive and easy to monitor and provide accurate contact stress measurements.

Thus, although the sensor element of this invention must be first implanted for conducting the in vivo measurements, it requires no external connections for its continued operation unlike other common stress or strain transducers. The stress applied to the sensor element is determined by a non-invasive NMR spectroscopic method. In fact, the gel contained in the sensor element may be viewed as a passive telemetry system which transmits its dilation to a remote receiver coil upon being interrogated by an RF pulse. The sensor may be sterilized prior to implantation to ensure full sterility. However, the absence of leads or wires emerging from the patient after the sensor element is implanted ensures extremely high probabilities of maintaining a sterile field therearound. The sensor element of this invention measures an equilibrium mechanochemical effect, and accordingly an excellent DC response is attained. Moreover, the sensor contains no cytotoxic substances or non-toxic chemicals whose release would present a threat to the surrounding biological tissues. The operating range and sensitivity of the sensor can be varied by a careful selection of the elements utilized in the manufacture of the sensor element itself. For instance, the composition of the gel and its physical and chemical properties (e.g., its stiffness, degree of cross-linking and relative amount of monomer components) may be varied to suit the needs of a particular application. In addition, the NMR-detectible agent utilized is not an endogenous substrate and can be easily detected since the tissues surrounding the implanted sensor element are NMR-transparent for the most part. Thus, very low background signal noise is encountered.

This invention provides a biological implantable pressure sensor element comprising a fixed volume pouch formed by a sealed, flexible, impermeable membrane comprising therewithin a gel mass contained in a gel volume, the gel being hydrated with an aqueous solution comprising an agent having at least a first and a second NMR-detectable form, the proportion of the first to the second form of said agent and said gel volume being determined by their electrolytic interaction with the gel, whereby when an external pressure is applied to the sensor element a d(chemical shift)/d($\sigma$/K) greater than about 0.0001 ppm, and more preferably greater than about 0.01 ppm and still more preferably about 0.1 to 10 ppm, is attained, whereby $\sigma$ is the external pressure and K is the modulus of the gel.

In a separate embodiment the gel mass can be surrounded by a softer, neutral or electrolyte gel and/or the NMR-detectable agent may be part of the polymeric structure of the gel.

The sensor element may be manufactured in any desired size and suited to the particular application it is intended for. Accordingly, if it is to be implanted in a small part of the human body it may be provided in a size ranging in diameter from about 0.01 to 1000 cm$^3$. For areas that are larger and can accommodate a larger device the sensor element may have a diameter of about 1000 to 10000 cm$^3$. The sensor element for utilization in vitro may be manufactured in any desired size and shape thus being adaptable for specific applications. One such example may be the sensor element of the invention being manufactured in a cylindrical form of a rather large circular diameter which could be used as the support for the growth of cells. Accordingly any size in which cell tissues are customarily manufactured are appropriate for the present sensor element. The same is true in terms of the shape of the sensor element for in vivo implantation. The element may be manufactured in any shape suitable to accommodate the implantation requirements of specific body sections.

In an embodiment exemplified in this patent, the NMR-detectable agent is a $^{19}$F compound. However, other NMR-detectable compounds may be utilized as suitable. Examples of compounds known at the present time are $^{19}$F-trifluoroethylanine, $^{31}$phosphoric acid and $^{13}$C-carbonic acid. However, other NMR-detectable agents are being manufactured al the time which provide higher sensitivity and more accurate measurements and those can be utilized as they become known.

In a particular embodiment of the present invention the NMR-detectable agent is charged. Suitable agents are weak acids and bases such as amino acids. However, other electrolytes may also be utilized which may or may not be physiologically acceptable since the agent is not placed in direct contact with body tissues. Examples of electrolytes suitable for use with the present invention are fluorinated amino acids such as difluromethylalanine, and the like.

FIG. 1 depicts a sensor element in accordance with the present invention which consists of an impermeable but flexible pouch containing a polyelectrolytic gel bathed in an aqueous solution. In operation, stress 1 is applied to a tissue 2. Tissue 2 is in contact with a sensor element in accordance with the invention shown to consist of a flexible membrane 3, containing an external bath 4, and a gel mass 5. The sensor is shown in the figure to be in touch with a tissue 6 which may in turn be subjected to stress 7 from the opposite side.

FIG. 5 shows a test device built in accordance with the present invention. The end of a 20 cm$^2$ plastic syringe 8 is sealed with paraffin tape. Holes 13 are drilled through the rubber tamper 12 of the syringe so that fluid can flow through the tamper when the plunger 9 of the syringe is depressed. The syringe is filled with gel 14 and the indicator solution or external bath 11 and then placed in an RF coil in the core of a magnet. Valves 14 connect tubes a and b to the interior of the syringe(s) and allow for remote control of pressure without manipulation of the plunger 9.

The pouch of the sensor element is formed of a sealed membrane which is flexible and impermeable. Suitable membrane materials are polyethylene, urethane and polyurethane, among others. However, other materials having these characteristics are known in the art and are also suitable for manufacturing the present device. In a particularly useful embodiment of the sensor element of the invention for in vivo utilization the membrane comprises a non-biodegradable, physiologically-acceptable membrane material. However, other materials having similar characteristic may also be utilized herein.

The gel of the sensor element of the invention may be formed from a monomer by polymerization and/or crosslinking thereof. Typically, a polymerizable monomer is selected and various polymerization and/or crosslinking degrees are tested in order to obtain a gel having the desired modulus characteristics. A suitable material for the gel is polyacrylamide. Once polymerized and/or crosslinked, the polymers may be partially degraded and/or hydrolyzed in order to attain the desired charge density characteristics thereof. Suitable gel materials are partially hydrolyzed polyacrylamide, and the like. However, other materials having similar characteristics may also be utilized.

Although the sensor element of the invention may be manufactured in a variety of forms, shapes and consistencies, a generally suitable device is that where a proportion of gel:solution in the pouch is about 1:10 to 10:1, more preferably about 1:8 to 8:1, and still more preferably about 1:5 to 5:1. Also, in general the NMR-detectable agent is present in the aqueous solution contained in the touch in an amount of about $1\times10^{-5}$ to 3.0M, and preferably about $5.0\times10^{-3}$ to $1\times10^{-2}$M. However, other concentrations of the NMR-detectable agent may be utilized as suitable for optimal detection taking into consideration the distance between the implantation site and the NMR source and detector as well as the loss of signal due to the implantation depth.

The sensor element comprises an impermeable but flexible pouch that contains a gel in an ionic solution. However, other ions may be present in the aqueous solution and as pH defining ions and the like and a softer gel may surround the central gel core. FIG. 1 shows a schematic diagram of the pouch, the external solution and the gel.

One embodiment of the invention is set forth in the examples. The gel used in the examples is hydrolyzed polyacrylamide that is hydrated in an aqueous cocktail (pH 7.5) containing Na$^+$, Cl$^-$ and difluoromethylalanine-hydrochloride as the NMR-detectable agent. The latter is a sensitive pH indicator used to measure intercellular and intracellular pH in vivo with $^{19}$F NMR spectroscopy. The charged groups on the polymeric backbone of the gel are ionized at pH 7.5. Thus, the equilibrium concentration of the mobile ions, e.g., ([Na$^+$], [OH$^-$], [H$^+$], [Cl$^-$], and the two charged species of the $^{19}$F NMR indicator,

[NH+3C(CH3)CHF2)COOH] and [NH2C(CH3)(CHF2)COO−], differ in the interstitial and external fluid compartments.

When a normal stress applied to the bag compresses the gel, fluid is squeezed from this sponge-like material into the surrounding bath. This decreases the volume of interstitial fluid and increases the charge density of the charged groups on the gel. A redistribution of the mobile co- and counter-ions, including H+, between the interstitial and external volumes is eventually achieved. The new equilibrium is reflected by, in this case, a change in pH of the interstitial and external volumes.

In other embodiments of the present invention the NMR-detectable agent may be sensitive to solution parameters affected by the gel other than pH, such as other ionic entities and the like. However, these parameters must undergo changes which are attributable to the contact pressure exerted on the device. These changes are detectable by measuring, e.g., the chemical shift or other characteristics, in the NMR spectrum of the indicator molecule or NMR-detectible agent. The change in chemical shift is herein related to the applied stress by a mathematical model described below or an empirically derived relationship between the chemical shift and applied stress provided herein.

Mathematic Model of the Sensor's Response to an Applied Stress

The present mathematical model attempts to relate the applied stress to the measured shift in the $^{19}F$ NMR spectrum of the sensor. Continuum mechanics is used to describe the behavior of the gel under loading while physical-chemistry is used to determine the chemical changes that these stresses induce. Finally, elementary quantum mechanics is used to determine how these chemical changes affect the frequency shifts in the $^{19}F$ NMR spectra. More specifically, an equation of the conservation of momentum and a constitutive law of the gel, with appropriate boundary conditions, expresses as the relationship between the applied stress and the dilatation of the gel. The equations of conservation of mass, electroneutrality, electrochemical equilibrium and equilibrium dissociation of each chemical species constitute the description of the chemical interactions between the gel and the external bath. These expressions can be simplified to a system of non-linear algebraic equations that are solved numerically for the parameter, e.g., the hydrogen ion concentrations, within the gel and in the external bath. Finally, equations that relate the shift in Larmor frequencies of the observed $^{19}F$ NMR spectrum to the degree of dissociation of the parameter indicator or NMR-detectible agent, e.g., pH indicator, complete the model.

The polymer network is assumed to satisfy the constitutive law of an isotropic, Hookean material in accordance with the following equation.

$$\sigma_{ij}^{gel} = K \frac{\partial u_\alpha}{\partial x_\alpha} \delta_{ij} + 2G \left( \epsilon_{ij} - \frac{1}{3} \frac{\partial u_\alpha}{\partial x_\alpha} \delta_{ij} \right) \tag{1}$$

wherein K is the bulk elastic modulus of the gel and G is its shear elastic modulus. For small deformations, the strain tensor, $\epsilon_{ij}$, is defined as $$\epsilon_{ij} = \frac{1}{2} \left( \frac{\partial u_j}{\partial x_j} + \frac{\partial u_i}{\partial x_i} \right).$$

Since the gel is assumed to be in mechanical equilibrium, the conservation of linear momentum of the gel takes the following form.

$$\frac{\partial \sigma_{ij}^{gel}}{\partial x_j} = 0 \tag{1a}$$

If the gel is assumed to be in the shape of a rectangular prism when a uniform compressive stress, $-\sigma_0$, is applied on two of its faces while the other four faces are stress-free and unconstrained the applied stress can be related to the dilatation of the sample by the following equation.

$$-\sigma_0 = 3K\epsilon$$

wherein $\epsilon$ is the dilatation, $\epsilon = \epsilon_{xx} + \epsilon_{yy} + \epsilon_{zz}$. For small deformations, this quantity is equal to the fractional change in gel network volume relative to its unstrained state that is produced by the applied stress obtained from the following equation.

$$\frac{\partial V}{V_0} = \frac{V - V_0}{V_0} = \epsilon \tag{3}$$

wherein V is the volume of gel in the deformed state and $V_0$ is the is the volume in the undeformed state.

Using equations 2 and 3 together, we can relate the stress applied to the gel can be related to its volume as follows.

$$-\sigma_0 = 3K \left( \frac{V - V_0}{V_0} \right) \tag{3a}$$

If the bulk modulus and the dilatation of the gel are known, equation 3a helps to calculate the magnitude of the compressive stress applied to the gel. It should be noted that equation (3a) is only valid for small deformations.

A mathematical relationship between the dilatation of the sample and the resultant chemical shift of an indicator molecule determined by $^{19}F$ NMR are derived hereinbelow.

The sensor element of the invention is modeled as two compartments that are in electrochemical equilibrium with one another. One compartment is the gel polymer network and its interstitial fluid and the other is the external solution contained in the pouch. Both compartments are enclosed by a flexible, indistensable membrane pouch that is impermeable to water and other ions but allows heat to be exchanged across its walls. This pouch is assumed to lie in an infinite temperature reservoir.

Since no matter is exchanged across the impermeable barrier, the equation of the conservation of mass of each species within the bag takes the following form.

$$M_i = \sum_{j=1}^{N_c} V_j [C_i]_j. \tag{4a}$$

wherein $M_i$ is the moles of the $i^{th}$ constituent molecule, $[C_i]_j$ is the concentration of the $i^{th}$ constituent molecule in the $j^{th}$ compartment, $V_j$ is the volume of the $j^{th}$ compartment and $N_c$ (2 in this case) is the total number of compartments. Since the number of moles of each species in solution is prescribed by the artisan, all of the $M_i$ can be treated as constants in the model. As such, equation (4a) constitutes a set of constraint equations.

An additional constraint equation is provided when the condition that the contents of the pouch are individually incompressible is applied so that the total volume of the sensor, $V_T$, remains constant as can be seen from the following equation.

$$V_T = \sum_{j=1}^{N_c} V_j$$

The condition of macroscopic electroneutrality in each compartment imposes yet another constraint. If $Z_i$ is the valence number of the $i^{th}$ constituent molecule and $N_j$ is the total number of charged species present in compartment j, then $$0 = \sum_{i=1}^{N_j} [C_i]_j Z_i. \tag{4}$$

Although this discussion is restricted to a two-compartment system, these formulas can be extended to model multi-compartment systems as well It is herein assumed that the sensor is in thermodynamic equilibrium and there is no net flux of water or ions between compartments. Under these conditions the Folker-Plank equation results in the well-known Donnan equilibrium equations (5).

$$\left(\frac{[C_i]_1}{[C_i]_2}\right) Z_i = \left(\frac{[C_k]_1}{[C_k]_2}\right) Z_k \tag{5}$$

where i and k denote any two mobile ionic species.

The carboxylic acid groups that are covalently bonded to the backbone of the exemplary gel are modeled as a monoprotic weak acid, HP, whose dissociation is governed by the following chemical formula.

$$HP + H_2O <=> H_3O^+ + P^-$$

where $[P^-]$ is the concentration of ionized groups in the interstitial solvent. The weak acid obeys the following equilibrium dissociation relationship $$K_a' = \frac{[P^-][H_3O^+]_2}{[HP]} \tag{5a}$$

wherein $K_a'$ is the acid dissociation constant.

The total concentration of ionizable groups, $[P_{tot}]$, is therefore $$[P_{tot}] = [P^-] + [HP]. \tag{5b}$$

By combining equations (5a) and (5b) it is possible to express the concentration of ionized or fixed-charges in terms of the hydronium ion concentration $[H_3O^+]$ and the total concentration of ionizable groups in the network as follows.

$$[P^-] = [P_{tot}] \frac{K_a'}{K_a' + [H_3O^+]_2}. \tag{6}$$

Moreover, as the total number of ionizable groups in the polymer is conserved, equation (4a) becomes:

$$M_{P_{tot}} = V_{20}[P_{tot}]_0 = V_2 [P_{tot}]$$

wherein $V_{20}$ is the volume of the gel in its undistended state and $[P_{tot}]_0$ is the corresponding concentration of ionizable groups when the applied stress is zero. The dissociation of water is also required to obey the following familiar equation.

$$[H_3O^+]_1[OH^-]_1 = K_W' = [H_3O^+]_2[OH^-]_2 \tag{7}$$

For the particular chemical system used in the exemplary tests, the equations of electroneutrality become $$[H_3O^+]_1 + [Na^+]_1 + [NH_3{}^{30} - R - COOH]_1$$
$$- [OH^-]_1$$
$$- [Cl^-]_1 - [NH_2 - R - COO^-]_1 = 0 \tag{8}$$

for compartment 1, and $$[H_3O^+]_2 + [Na^+]_2 + [NH_3{}^+ - R - COOH]_2$$
$$- [OH^-]_2$$
$$- [Cl^-]_2 - [NH_2 - R - COO^-]_2 - [P^-] = 0 \tag{9}$$

for compartment 2.

Because indicators are usually present in trace concentrations, their effect is often neglected in typical acid/base calculations. Since millimolar concentrations of indicator or NMR-detectible agent may be used to improve the signa/noise ratio of the spectroscopic measurement its dissociation reactions must also be included in this model.

Once dissolved in solution, the amphoteric $^{19}F$ NMR indicator dissociates in a two-step reaction which may be described as follows.

$$NH_3{}^+ - R - COOH + H_2O \rightleftharpoons NH_3{}^+ - R - COO^- + H_3O^+;$$

with $K_1' = \dfrac{[NH_3{}^+ - R - COO^-][H_3O^+]}{[NH_3{}^+ - R - COO^-]}$ and $$NH_3{}^+ - R - COO^- + H_2O \rightleftharpoons NH_2 - R - COO^- + H_3O^+;$$

with $K_2' = \dfrac{[NH_2 - R - COO^-][H_3O^+]}{[NH_3{}^+ - R - COO^-]}$

The total number of moles of indicator is then $$M_{ind} = V_1([NH_3{}^+ - R - COO^-]_1 + [NH_3{}^+ - R - COOH]_1 + [NH_2 - R - COO^-]_1)$$
$$+ V_2([NH_3{}^+ - R - COO^-]_2 + [NH_3{}^+ - R - COOH]_2 + [NH_2 - R - COO^-]_2)$$

The electrically neutral Zwitterion, $NH_3{}^+ - R - COO^-$, is a small molecule that can move freely between compartments At equilibrium it is assumed to be present in equal concentrations in each compartment:

$$[NH_3{}^+ - R - COO^-]_1 = [NH_3{}^+ - R - COO^-]_2.$$

After various substitutions, equations (8) and (9) can be placed in the following forms.

$$h_1([H_3O^+]_1, [H_3O^+]_2) = 0 \quad (10)$$

$$h_2([H_3O^+]_1, [H_3O^+]_2) = 0 \quad (11)$$

wherein $h_1$ and $h_2$ each are scalar functions whose exact form is given below. These two equations now contain only two dependent variables, $[H_3O^+]_1$ and $[H_3O^+]_2$. The other quantities are either independent variables that can be prescribed by the artisan or material constants whose values are known a priori by independent measurements. The stress is treated as a free parameter. Therefore, equations (10) and (11) constitute a system of two non-linear, algebraic equations with two unknowns which can be solved using standard numerical techniques, such as the Levenberg algorithm Numerical routines used to solve a system of non-linear algebraic equations are provided in the IMSL Library of Scientific Subroutines, Version 1.0, IMSL, Houston, Tex.; "Numerical Recipes" by Press, Flannery et al, Cambridge Press (1986).

Figure 2:
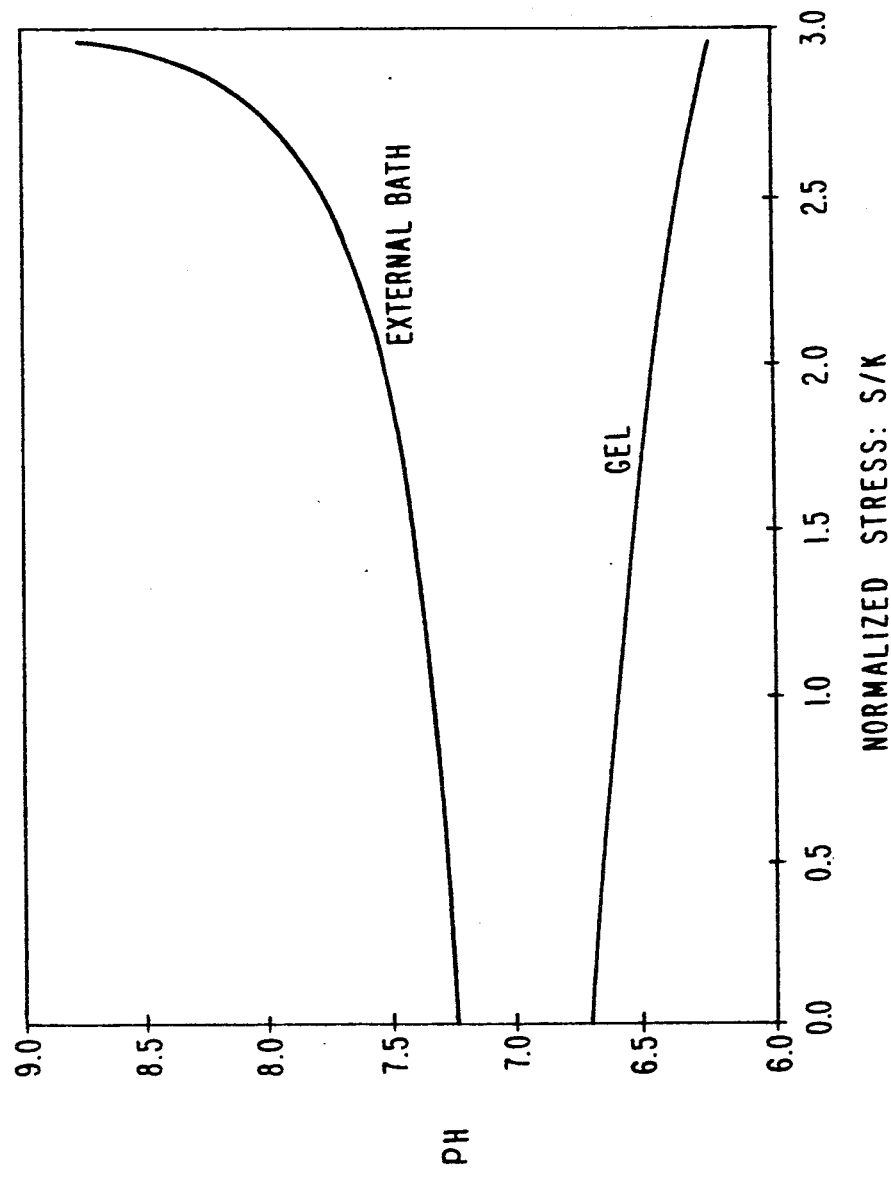
FIG. 2 shows the functional relationship between interstitial and external pH of the aqueous solution and an applied stress onto the sensor element. This is an "equilibrium stress titration curve" which shows the close analogy between chemical and mechanical titration. An equilibrium results between the internal and external gel pH from slowly increasing the applied stress on the sensor element. The value of the stress applied is normalized by dividing the stress by the bulk modulus of the gel ($\sigma/K$, which is dimensionless).

A similar treatment may be applied to obtain a change in a parameter other than pH which is caused by contact pressure applied to the sensor element of the invention. FIG. 2 shows the calculated relationship between the parameter in, e.g., pH, in both the external and internal bath and the normalized applied stress. The stress, $\sigma$, is normalized by the bulk modulus of the gel, K, therefore making the ratio, $\sigma/K$, dimensionless. This figure is aptly titled "stress titration curve" because of the close analogy that exists between mechanical and chemical titration experiments It shows the predicted equilibrium interstitial and external solution parameter, e.g., pH, that would result from increasing the applied stress on the gel reversibly (i.e., maintaining the system in electromechanochemical equilibrium). The difference in the parameter, e.g., pH, between the interstitial and external solutions at equilibrium is obtained from the Donnan equations.

Figure 3:
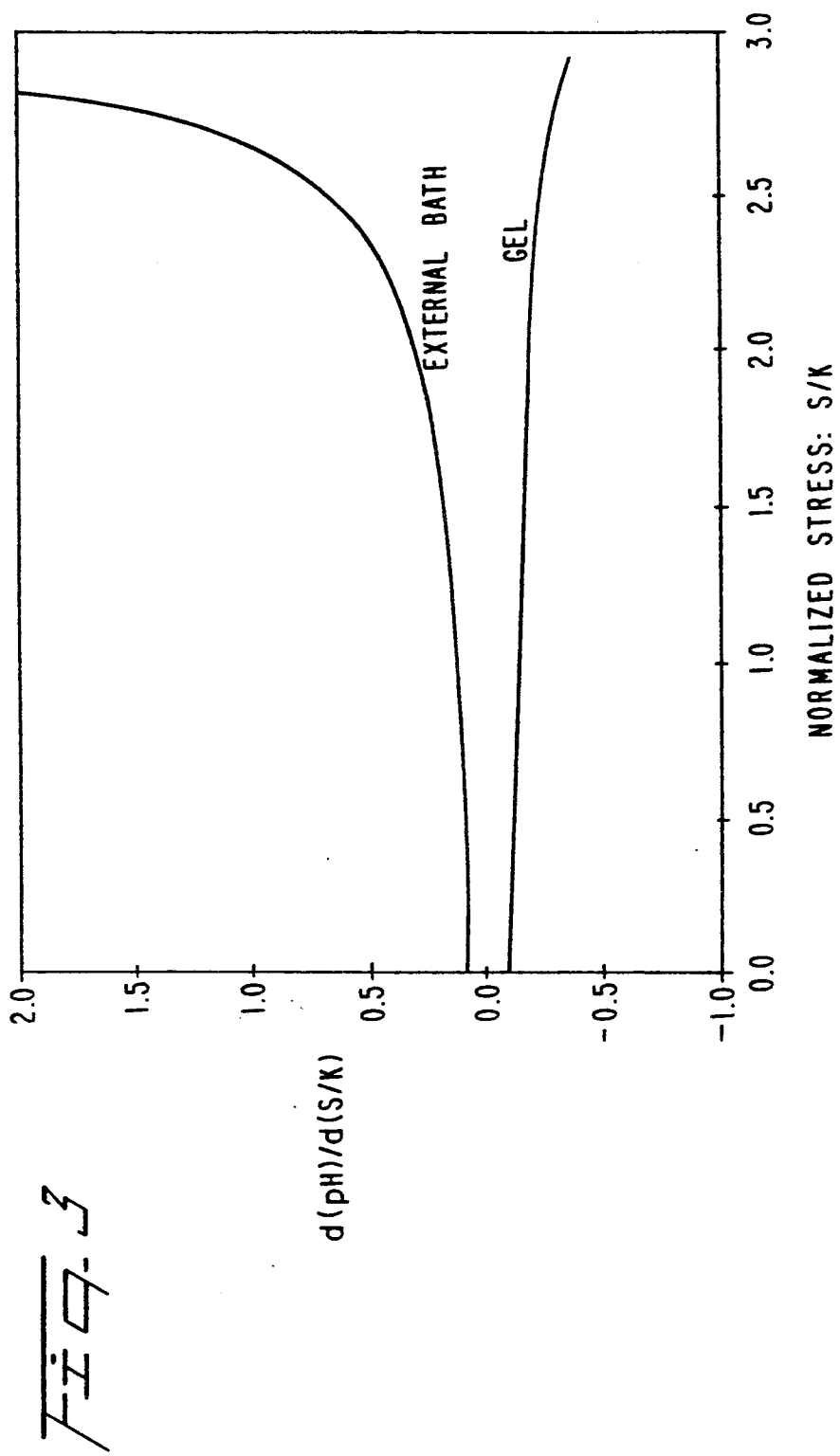
FIG. 3 depicts the stress sensitivity of a sensor element in accordance with the invention. In the figure the variation of the pH with the normalized stress in the interstitial and external gel fluid volume can be seen. The sensitivity of the sensor element can be calculated by taking the derivative of the pH v. $\sigma/K$ curve with respect to the normalized stress.

The sensitivity of the gel sensor element is given by the slope of the parameter, e.g., pH, vs. $\sigma/K$ curve. It is calculated by numerically differentiating the curves of the parameter, e.g., pH, vs. $\sigma/K$ curve with respect to $\sigma/K$ using a centered differences formula. The results are shown in FIG. 3. In the expected operating range of the exemplified sensor (i.e., $\sigma/K <$ about 1) its sensitivity is approximately 0.25 pH units per unit change in the normalized stress. The sensitivity and range of the gel are controlled by several independent variables: the polymer content, the degree of crosslinking, the number of ionizable groups and the bulk modulus, K, among others.

The equations given above can be used to determine the applied stress from the gel interstitial and external concentrations of any of the mobile ionic species. Such measurements can be performed using ion selective electrodes or colormetric indicators, for example. In order to determine these concentration differences using $^{19}F$ NMR spectroscopy, another relationship must be derived between the chemical shift observed in the $^{19}F$ NMR spectrum and the concentration of mobile ions within each compartment of the sensor. Determination of the $^{19}F$ NMR Chemical Shift from the Distribution of $[H_3O^+]_1$ and $[H_3O^+]_2$:

The indicator, a difluorinated amino acid, can exist in one of three dissociation states. It will be shown that the relative population of each state reflects the ambient pH. Since the chemical shift differs for each state, the measured chemical shift is shown to be predictably related to pH.

The lifetime of a particular is on the order of its inverse dissociation rate constant whereas the time it precesses in the magnetic field equals its inverse Larmor frequency. The rate constant of dissociation is proportional to $\exp(-\Delta G^*/kT)$ where $\Delta G^*$ is the activation energy of the state, k is the Boltzmann constant and T is the absolute temperature. For the deprotonation reaction of an amine group, the rate constant $\sim O(10^6)$ Hz. However, the relevant frequency of the acquistion of the spectrum is $(\nu_a - \nu_b)/2$ where $\nu_a$ and $\nu_b$ are the Larmor frequencies $\nu$ of one of the Fluorine moieties in the protonated and deprotonated states, respectively. For this indicator, this frequency difference is $O(10^2)$ Hz. Therefore, the indicator changes its state an average of 1000 times during the time an individual $^{19}F$ NMR spectrum is acquired. In this rapid exchange limit, the measured chemical shift spectrum of each dissociation state of the indicator molecule, i, weighed by its probability of occurrence, $p(i)_1$. The indicator used in these experiments exhibits three separate dissociation states, so the chemical shift is given as:

$$E(I_1,I_2,I_3I_4)_1 = p(0)_1(I_1,I_2,I_3,I_4)_1^{(0)} + p(-1)_1(I_1,I_2,I_3,I_4)_1^{(-1)} + p(+1)_1(I_1,I_2,I_3,I_4)_1^{(+1)} \quad (11a)$$

The components of the vector, $(I_1, I_2, I_3, I_4)_1$ represent the peaks of the four chemical shift lines (Hz) which comprise the quartet observed in the $^{19}F$ NMR spectrum. Since the measured chemical shift is shown to be a mathematical expectation it is denoted as $E(I_1, I_2, I_3, I_4)_1$. The probability of a particular state, i, is just its relative concentration in solution:

$$p(i)_1 = \left( \frac{[IND^i]_1}{[IND_{tot}]_1} \right) \quad (11b)$$

Therefore, the measured chemical shift can be expressed in terms of the chemical shift of the different states of the indicator and their respective relative concentrations:

$$E(I_1, I_2, I_3, I_4)_1 = \left( \frac{[IND^0]_1}{[IND_{tot}]_1} \right)(I_1, I_2, I_3, I_4)_1^{(0)} + \left( \frac{[IND^-]_1}{[IND_{tot}]_1} \right)(I_1, I_2, I_3, I_4)_1^{(-1)} + \left( \frac{[IND^+]_1}{[IND_{tot}]_1} \right)(I_1, I_2, I_3, I_4)_1^{(+1)} \quad (12)$$

An analogous expression can be written for the second compartment that is communicating with the first:

$$E(I_1, I_2, I_3, I_4)_2 = \left( \frac{[IND^0]_2}{[IND_{tot}]_2} \right)(I_1, I_2, I_3, I_4)_2^{(0)} + \left( \frac{[IND^-]_2}{[IND_{tot}]_2} \right)(I_1, I_2, I_3, I_4)_2^{(-1)} + \left( \frac{[IND^+]_2}{[IND_{tot}]_2} \right)(I_1, I_2, I_3, I_4)_2^{(+1)}$$

It has been observed that the measured difference, $E(I_2-I_3)$, is sensitive to pH changes. A formula for this difference signal is obtained from equation (20):

$$E(I_2 - I_3)_i = \left(\frac{[IND^0]_i}{[IND_{tot}]_i}\right)(I_2 - I_3)_i^{(0)} + \quad (13a)$$

$$\left(\frac{[IND^-]_i}{[IND_{tot}]_i}\right)(I_2 - I_3)_i^{(-1)} + \left(\frac{[IND^+]_i}{[IND_{tot}]_i}\right)(I_2 - I_3)_i^{(+1)}$$

Figure 4:
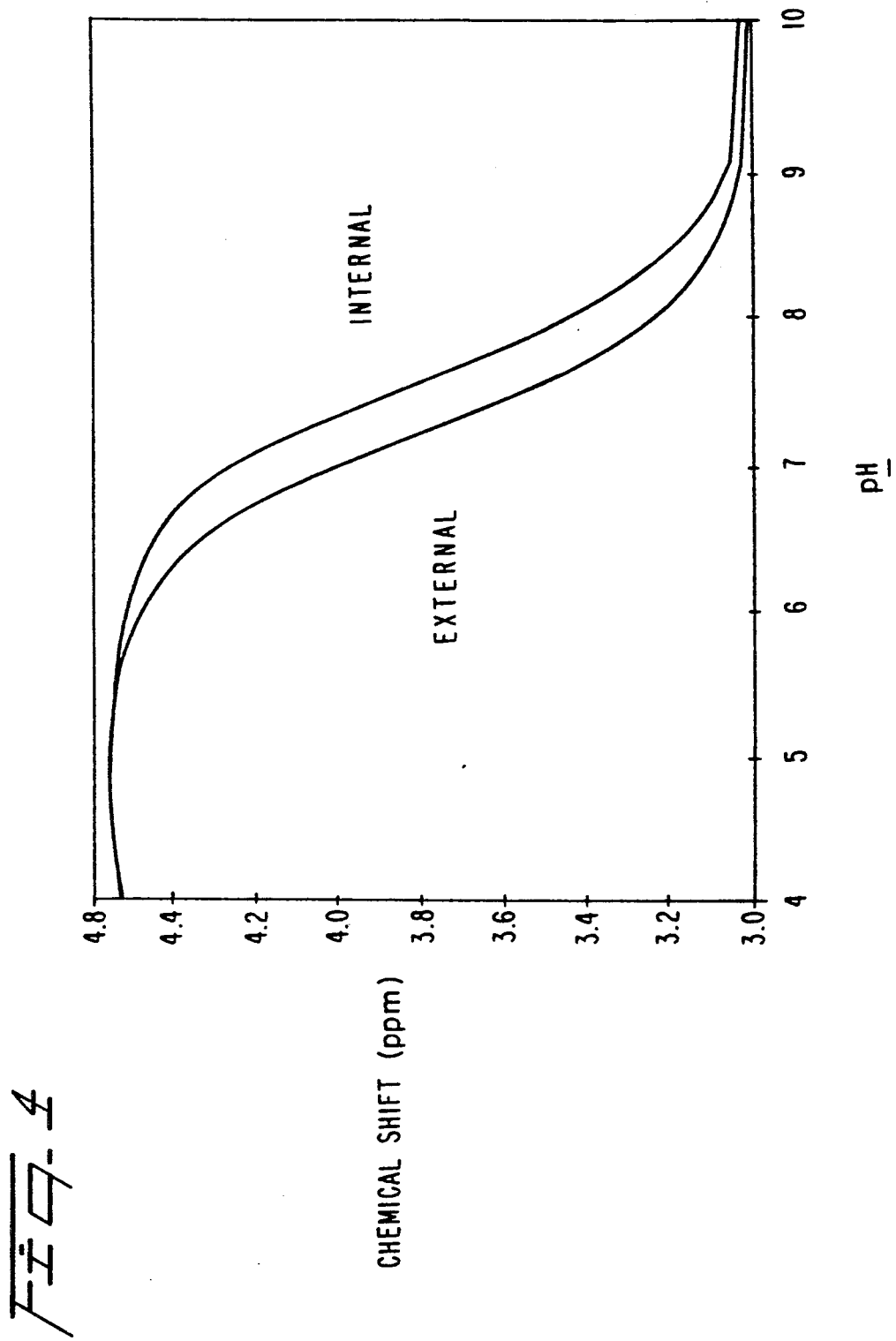
FIG. 4 shows the variation of the chemical shift of the NMR-detectible agent present in the sensor device in accordance with the invention with pH variations in the external solution and/or the gel volume within the device.

FIG. 4 shows the calculated values of $I_2-I_3$ (ppm) plotted against pH for both the external and interstitial solutions The relative concentrations of the indicator were obtained from equations 13 and 14. Once the hydronium ion concentration is known in both compartments, the concentration of each of the indicator species was determined using equations 12a-d. In preparing FIG. 4, values of $I_2-I_3$ in the Zwitterionic and negatively charged states were estimated from Deutsch et al. In the pH range at which the sensor is maintained, the indicator exists primarily in the Zwitterionic and negatively charged forms so that the last term in equation (20a) could be neglected.

In the operating range of this sensor element, the indicator exists primarily in the Zwitterionic and negatively charged form states. Therefore, the last terms in equations 12 and 13 can be neglected.

The time it takes for the indicator to diffuse between compartments scales with $\delta^2/D$ where $\delta$ is a characteristic length and $D$ is the diffusivity of the indicator molecule in water. For this sensor element $D \sim 0.9 \times 10^{-5}$ cm$^2$/sec$^{20}$ and $\delta \sim 0.1$ cm so that $\delta^2/D \sim 1000$ sec. Since the diffusion time is much greater than $2/(\nu_a-\nu_b) \sim 0.01$ sec, it can be assumed that the indicator molecules will remain in their respective compartments while the spectrum is measured. This implies that the spectrum from a two-compartment system will be the superposition of the spectra from each compartment. Since the strength of the signal is proportional to the mass of the indicator, the measured spectrum will be proportional to the spectra from compartments 1 and 2 weighted by their respective volumes:

$$(I_1,I_2,I_3,I_4)_m \sim [IND_{tot}]_1 V_1(I_1,I_2,I_3,I_4)_1 + [IND_{tot}]_2 V_2(I_1,I_2,I_3I_4)_2 \quad (14)$$

FIG. 7 illustrates this last point It shows a typical measured $^{19}$F NMR spectrum of the gel and the external bath The two distinct quartets, marked i and o (standing for interstitial and external, respectively) are superposed.

Similar calculations can be made for parameters other than pH or hydronium concentration to determine the extent of their changes brought about by a transversal pressure being applied to the sensor element of the invention.

Determination of the Material Constants of the Gel

There are several parameters whose values can be prescribed a priori or measured directly. These include the dissociation constants of water, the polyelectrolyte gel, and the $^{19}$F NMR indicator, the polymer volume, the material's bulk modulus, and the number and concentration of ionizable groups and the diffusivity of the indicator.

Also part of this invention is a kit comprising 1 to 100 sensor elements which may be sterilized and individually wrapped.

Also provided herein is a method of measuring in vivo contact stress applied to an implanted pressure sensor element, comprising (a) implanting the pressure sensor of the invention into a situs of a subject in need of such measurement;

(b) non-invasively subjecting the subject situs to a nuclear magnetic resonance source effective to detect said NMR-detectible agent;

(c) obtaining the NMR spectrum of said agent;

(d) obtaining the chemical shifts from the spectrum;

(e) repeating steps (b) to (d) at least once at a desired time interval;

(f) comparing the chemical shifts obtained in step (d) at different time intervals; and (g) calculating the contact stress applied to said sensor element at a desired time from a correlation or calibration curve relating the observed chemical shift to the normalized stress applied to the sensor element.

The implantation of the sensor is conducted in accordance with known techniques in the art. These techniques should be sterile and conducted with utmost care in order for the implanted device to be safely lodged in a desired site. Care must also be exercised to close the implantation site in complete sterility to ensure the safe long-term implantation of the present device.

There are various manners in which NMR spectra can be obtained and those are known in the art. Any of these techniques can be utilized for practicing the present invention.

Steps (b) through (d) may be conducted as many times as desired in order to obtain point comparisons in time or to follow the status of a particular patient as needed. The time intervals may be as close as seconds apart and as far apart as days, weeks, months or years.

The sensor element of the invention may be removed after being implanted if it is determined that it is no longer necessary to follow up a localized pathological development. The removal is undertaken by surgical procedures known in the art.

The comparison of the chemical shifts obtained in step (d) of the present method may also be conducted by methods known in the art.

Thereafter, the contact stress applied to said sensor element at a desired time may be calculated from a correlation or calibration curve relating the observed chemical shift to the normalized stress applied to the sensor element. One such example appears in the following table.

TABLE 1

| Calibration Curve for Sensor Element of the Invention | | |
|---|---|---|
| Normalized Stress ($\sigma/K$) | Chemical Shift (ppm) External Compartment | Chemical Shift (ppm) Interstitial Compartment |
| 0.0000000000000000E + 00 | 4.391586151032058 | 4.522367371313221 |
| 1.4851485379040241E − 02 | 4.389266576446108 | 4.522135822243916 |
| 2.9702970758080482E − 02 | 4.386894352624341 | 4.521899367304929 |
| 4.4554457068443298E − 02 | 4.384468000324444 | 4.521657849898495 |
| 5.9405941516160965E − 02 | 4.381985991428452 | 4.521411106774711 |
| 7.4257425963878632E − 02 | 4.379446745475916 | 4.521158967532215 |
| 8.9108914136886597E − 02 | 4.376848627932138 | 4.520901254271981 |
| 0.1039603948593140 | 4.374189950936039 | 4.520637781481854 |
| 0.1188118830323219 | 4.371468963653133 | 4.520368354874742 |
| 0.1336633712053299 | 4.368683858416777 | 4.520092771774425 |
| 0.1485148519277573 | 4.365832764249117 | 4.519810820231108 |
| 0.1633663326501846 | 4.362913741142973 | 4.519522278193044 |
| 0.1782178282737732 | 4.359924778319357 | 4.519226913048662 |
| 0.1930693089962006 | 4.356863801837395 | 4.518924482067234 |
| 0.2079207897186279 | 4.353728653359045 | 4.518614729962164 |
| 0.2227722704410553 | 4.350517098645519 | 4.518297389362498 |

TABLE 1-continued
Calibration Curve for Sensor Element of the Invention

| Normalized Stress ($\sigma/K$) | Chemical Shift (ppm) External Compartment | Chemical Shift (ppm) Interstitial Compartment |
|---|---|---|
| 0.2376237660646439 | 4.347226817632364 | 4.517972179431002 |
| 0.2524752616882324 | 4.343855410462412 | 4.517638806023369 |
| 0.2673267424106598 | 4.340400387246609 | 4.517296960200471 |
| 0.2821782231330872 | 4.336859156613720 | 4.516946316755536 |
| 0.2970297038555145 | 4.333229031362762 | 4.516586533305093 |
| 0.3118811845779419 | 4.329507220321184 | 4.516217250662992 |
| 0.3267326653003693 | 4.325690823258127 | 4.515838089857938 |
| 0.3415841460227966 | 4.321776825490946 | 4.515448651756092 |
| 0.3564356565475464 | 4.317762084005046 | 4.515048514685721 |
| 0.3712871372699738 | 4.313643353808439 | 4.514637236174988 |
| 0.3861386179924011 | 4.309417233156625 | 4.514214346515224 |
| 0.4009900987148285 | 4.305080188718033 | 4.513779350192480 |
| 0.4158415794372559 | 4.300628540337361 | 4.513331723186497 |
| 0.4306930601596832 | 4.296058453292660 | 4.512870910895181 |
| 0.4455445408821106 | 4.291365930051765 | 4.512396325875326 |
| 0.4603960514068604 | 4.286546791696196 | 4.511907344384246 |
| 0.4752475321292877 | 4.281596707504355 | 4.511403307646468 |
| 0.4900990128517151 | 4.276511126975329 | 4.510883513032686 |
| 0.5049505233764648 | 4.271285296981563 | 4.510347213649311 |
| 0.5198019742965698 | 4.265914294031907 | 4.509793619319675 |
| 0.5346534848213196 | 4.260392894613094 | 4.509221880625205 |
| 0.5495049357414246 | 4.254715724710684 | 4.508631101427669 |
| 0.5643564462661743 | 4.248877068583150 | 4.508020315829301 |
| 0.5792078971862793 | 4.242871036324180 | 4.507388502016967 |
| 0.5940594077110291 | 4.236691360420059 | 4.506734556956984 |
| 0.6089109182357788 | 4.230331545800639 | 4.506057307660463 |
| 0.6237623691558838 | 4.223784782547839 | 4.505355497048957 |
| 0.6386138796806335 | 4.217043844250202 | 4.504627767374787 |
| 0.6534653306007385 | 4.210101252876398 | 4.503872671633165 |
| 0.6683168411254883 | 4.202949039623769 | 4.503088640630597 |
| 0.6831682920455933 | 4.195578943692932 | 4.502273996615836 |
| 0.6980198025703430 | 4.187982156364133 | 4.501426916178396 |
| 0.7128713130950928 | 4.180149497716269 | 4.500545439501254 |
| 0.7277227640151978 | 4.172071301813902 | 4.499627446211477 |
| 0.7425742745399475 | 4.163737282434994 | 4.498670626868532 |
| 0.7574257254600525 | 4.155136732789664 | 4.497672490153803 |
| 0.7722772359848022 | 4.146258198133166 | 4.496630310650084 |
| 0.7871286869049072 | 4.137089741839308 | 4.495541136573807 |
| 0.8019801974296570 | 4.127618595280836 | 4.494401728614706 |
| 0.8168317079544067 | 4.117831368878571 | 4.493208558533234 |
| 0.8316831588745117 | 4.107713894808518 | 4.491957760982756 |
| 0.8465346693992615 | 4.097251042341731 | 4.490645076161130 |

The method of the invention may also be practiced in a manner such that steps (d), (f) and (g) are computerized. This embodiment greatly speeds the generation of data.

The sensor element of the invention may be implanted in a variety of sites of a subject. Examples of these are between a tumor and its surrounding tissue, a tumor and an adjacent bone, in an articulated joint, in a swollen tissue, between two swollen tissues, between a muscle and a fascia and the like.

Also provided herein is a method of measuring in vitro contact stress applied to a pressure sensor element, comprising (a) placing the stress sensor element of the invention in contact with a biological tissue in culture;

(b) non-invasively subjecting the biological tissue to a nuclear magnetic resonance source effective to detect said NMR-detectible agent;

(c) obtaining the NMR spectrum of said agent;

(d) obtaining the chemical shifts from the spectrum;

(e) repeating steps (b) to (d) at least once at a desired time interval;

(f) comparing the chemical shifts obtained in step (d) at different time intervals; and (g) calculating the contact stress applied to said sensor element at a desired time from a correlation or calibration curve relating the observed chemical shift to the normalized stress ($\sigma/K$) for the sensor element.

In general the steps of this method may be practiced under the same condition as those for the method of measuring in vivo contact stress described above. However, in some cases different conditions may be suitable.

As in the previous case steps (d), (f) and (g) may be computerized in the practice of this method.

In a particular embodiment of this method, the biological tissue is a cell(s) which is (are) placed in contact with a sensor element and allowed to grow and proliferate in contact therewith to provide a layer of cells capable of applying a contact stress to the sensor element. Conditions under which the cells may be grown are known in the art and need not be described herein. Also known in the art are growth media in which cells may proliferate and form layers in a culture.

Having now generally described this invention the same will be better understood to certain specific examples, which are included herein for purposes of illustration only and which are not intended to be limiting of the invention or any embodiment thereof, unless so specified.

EXAMPLES

Example 1

Proton Spectra

FIGS. 5a and 5b depict the system used to demonstrate that an applied stress can cause a measurable chemical shift during an in vitro experiment with a phantom. The end of a 20 cm$^3$ plastic syringe is sealed with a paraffin tape. Holes are drilled through the rubber tamper so that fluid can flow across it when the plunger is depressed. The syringe is first filled with 3.0 ml of polyacrylamide gel (15% by weight), 50.0 mg of difluoromethylalanine hydrochloride (the $^{19}$F NMR —pH indicator) and 0.1 NaOH and distilled, deionized water to bring the total volume to 5.0 ml at pH 7.5. The cylindrical RF transmitting coil is first tuned. Then the syringe is placed in the coil and the entire assembly is inserted into the core of a 4.7 Tesla magnet (General Electric ***). Initially, no compressive force is applied to the plunger (corresponding to the configuration shown in FIG. 5a). Proton and $^{19}$F NMR spectra are obtained by using Free Induction Decay (FID) after the magnetic field gradients are shimmed with the sample in place.

The same sample is then subjected to an applied compressive force of approximately 1.0 Newton (a mean stress of approximately 0.32 N/cm$^2$) and then allowed to equilibrate for about 1 hour. This test is depicted in FIG. 5b. Interstitial fluid from the gel flows into the reservoir above the sample. However, the total volume of polymer and solvent is constant in both tests. Proton and Fluorine NMR spectrum were again obtained for the compressed sample.

Figure 6A:
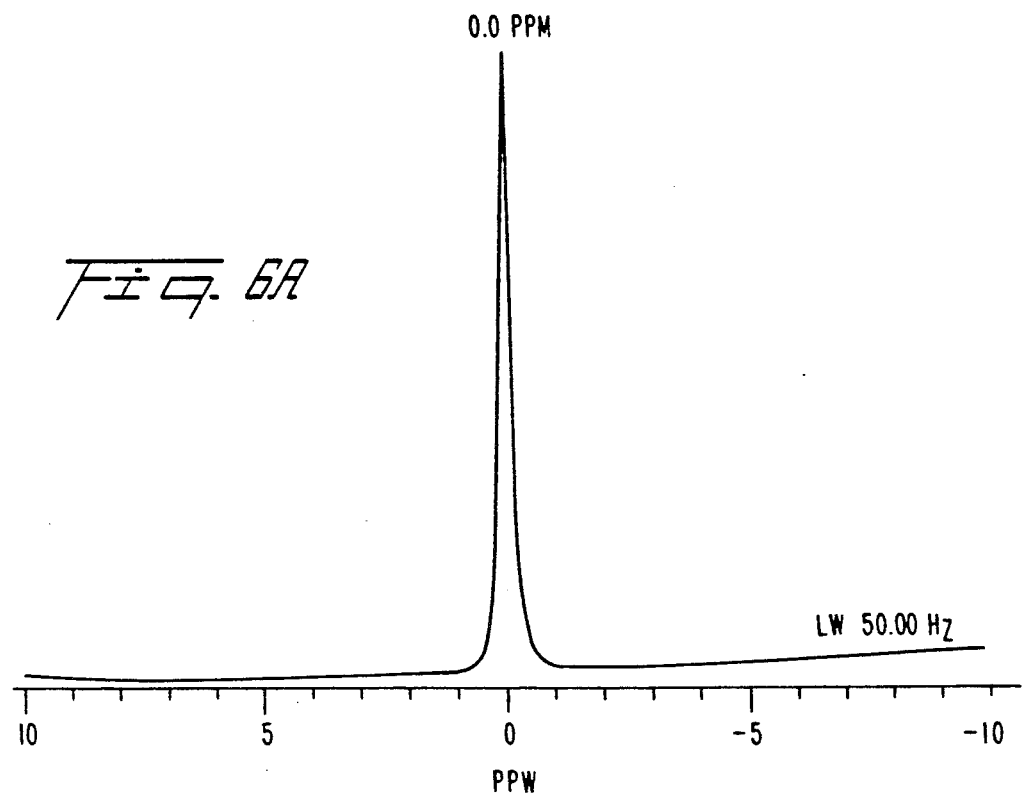
FIG. 6A shows the proton spectrum of the uncompressed sensor element and FIG. 6B shows the proton spectrum of the compressed sensor element.
Figure 6B:
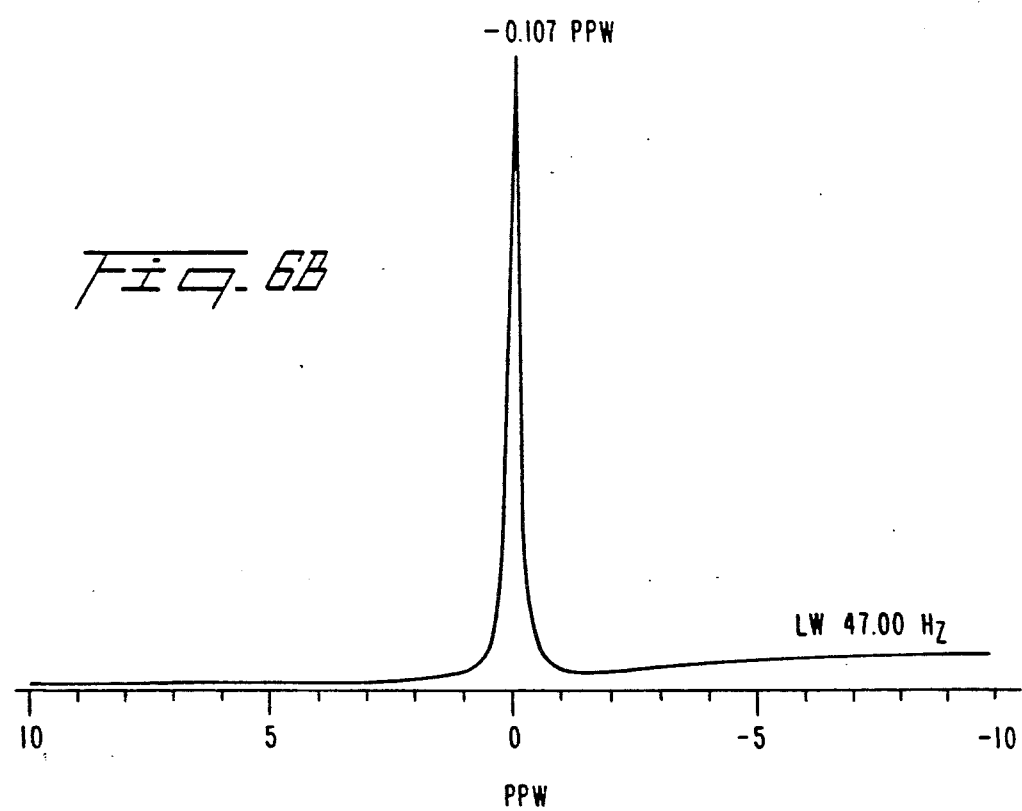

FIGS. 6a and 6b show the proton spectra obtained from the uncompressed and compressed gel samples, respectively.

EXAMPLE 2

Fluorine Spectra

FIG. 7 shows the Fluorine NMR spectrum of the uncompressed sample while FIG. 8 shows the Fluorine NMR spectrum of the compressed sample. The four sets of split peaks in the latter two figures are characteristic spectral lines of the Fluorine moiety, however, changes in the relative spacing between peaks (in ppm) reflect changes in ambient and internal pH.

EXAMPLE 3

Calibration curve of sensor element in accordance with the invention.

Prior to implantation a sensor element in accordance with this invention described above is calibrated under the following conditions. Before the sensor is implanted, a calibration table can be generated by placing the gel sensor in a "phantom", applying a set of known loads, and measuring the corresponding chemical shifts. The results shown in the table below are obtained.

TABLE 2

Calibration of Sensor Element of Example 1

| | A | B | C | D | E | F | G |
|---|---|---|---|---|---|---|---|
| 3 | AB system | quartet | analysis | | | | |
| 4 | | | | Performance: | Resolution: | 0.02408203 | ppm |
| 5 | | | | | Sensitivity | 5.91715976 | N/cm 2/ppm |
| 6 | $v_r$ (MHz) | 188.277038 | | | | | |
| 7 | | | | | spectral | 2C-J | |
| 8 | | line number | $(v - v_r)/v_r$ | $v - v_r$ | line height | L2-L3 | L2-L3 |
| 9 | | | ppm | Hz | cm | Hz | ppm |
| 10 | uncompressed | | | | | | |
| 11 | | L4 | −3.137 | −590.62507 | 5.8 | 799.989134 | 4.249 |
| 12 | | L3 | −1.961 | −369.21127 | 10 | | |
| 13 | | L2 | 2.288 | 430.777863 | 9 | | |
| 14 | | L1 | 3.467 | 652.756491 | 6.11 | | |
| 15 | | | | | | | |
| 16 | | L4' | −3.423 | −644.4723 | 5.5 | 695.871932 | 3.696 |
| 17 | | L3' | −1.681 | −316.4937 | 10.1 | | |
| 18 | | L2' | 2.015 | 379.378232 | 10.1 | | |
| 19 | | L1' | 3.746 | 705.285784 | 5.05 | | |
| 20 | | | | | | | |
| 21 | compressed | | | | | | |
| 22 | | L4 | −3.203 | −603.05135 | 6.3 | 768.170315 | 4.08 |
| 23 | | L3 | −2.002 | −376.93063 | 9.6 | | |
| 24 | | L2 | 2.078 | 391.239685 | 9.95 | | |
| 25 | | L1 | 3.265 | 614.724529 | 6.1 | | |
| 26 | | | | | | | |
| 27 | | L4' | −3.487 | −656.52203 | 5.1 | 668.760039 | 3.552 |
| 28 | | L3' | −1.73 | −325.71928 | 10.1 | | |
| 29 | | L2' | 1.822 | 343.040763 | 10 | | |
| 30 | | L1' | 3.538 | 666.12416 | 5.85 | | |

I claim:

1. A method of measuring in vivo contact stress applied to an implanted pressure sensor element which comprises:
    (a) implanting a pressure sensor element into a situs of a subject, said pressure sensor element having an NMR spectrum which changes in response to pressures applied to said pressure sensor element;
    (b) non-invasively subjecting the subject situs to a nuclear magnetic resonance source to obtain an NMR spectrum of said pressure sensor element; and
    (c) determining in vivo contact stress applied to said pressure sensor element from said NMR spectrum obtained in step (b).

2. The method of claim 1, wherein the pressure sensor element is implanted between a tumor and its surrounding tissue.

3. The method of claim 1, wherein the pressure sensor element is implanted between a tumor and an adjacent bone.

4. The method of claim 1, wherein the pressure sensor element is implanted in an articulated joint.

5. The method of claim 1, wherein the pressure sensor element is implanted into a swollen tissue.

6. The method of claim 1, wherein the pressure sensor element is implanted between two swollen tissues.

7. The method of claim 1, wherein the pressure sensor element is implanted between a muscle and a fascia.

8. A method of monitoring in vivo contact stress applied to an implanted pressure sensor element which comprises:
    (a) implanting a pressure sensor element into a situs of a subject, said pressure sensor element having an NMR spectrum which changes in response to pressure applied to said pressure sensor element;
    (b) non-invasively subjecting the subject situs to a nuclear magnetic resonance source at a first time, $t_1$, to obtain an NMR spectrum of said pressure sensor element at said first time, $t_1$;
    (c) determining in vivo contact stress applied to said pressure sensor element at said first time, $t_1$, from said NMR spectrum obtained in step (b);
    (d) non-invasively subjecting the subject situs to a nuclear magnetic resonance source at a second time, $t_2$, to obtain an NMR spectrum of said pressure sensor element at said second time, $t_2$, wherein $t_2 > t_1$;
    (e) determining in vivo contact stress applied to said pressure sensor element at said second time, $t_2$, from said NMR spectrum obtained in step (c); and
    (f) comparing said in vivo contact stress obtained in steps (c) and (e).

9. The method of claim 8, wherein the pressure sensor element is implanted between a tumor and its surrounding tissue.

10. The method of claim 8, wherein the pressure sensor element is implanted between a tumor and an adjacent bone.

11. The method of claim 8, wherein the pressure sensor element is implanted in an articulated joint.

12. The method of claim 8, wherein the pressure sensor element is implanted into a swollen tissue.

13. The method of claim 8, wherein the pressure sensor element is implanted between two swollen tissues.

14. The method of claim 8, wherein the pressure sensor element is implanted between a muscle and a fascia.

15. The method of claim 8, wherein the difference between $t_2$ and $t_1$ ranges from several seconds to several years.

* * * * *